United States Patent [19]

Junghans

[11] Patent Number: 4,507,238
[45] Date of Patent: Mar. 26, 1985

[54] PROCESS FOR THE PREPARATION OF 3-($\Delta^4$-3-KETOSTEROID-17α-YL)PROPIONIC ACID LACTONES

[75] Inventor: Klaus Junghans, Berlin, Fed. Rep. of Germany

[73] Assignee: Schering Aktiengesellschaft, Berlin and Bergkamen, Fed. Rep. of Germany

[21] Appl. No.: 582,644

[22] Filed: Feb. 22, 1984

[30] Foreign Application Priority Data

Feb. 22, 1983 [DE] Fed. Rep. of Germany ....... 3306554

[51] Int. Cl.³ .............................................. C07J 21/00
[52] U.S. Cl. .............................. 260/239.57; 260/397.4
[58] Field of Search .................................... 260/239.57

[56] References Cited

U.S. PATENT DOCUMENTS 4,057,543 11/1977 Dryden, Jr. et al. .......... 260/239.57
4,058,522 11/1977 Ke Kesy et al. ................ 260/239.57
4,129,564 12/1978 Wiechert et al. .............. 260/239.57

*Primary Examiner*—Elbert L. Roberts

*Attorney, Agent, or Firm*—Millen & White

[57] ABSTRACT

A simple process for preparing 3-($\Delta^4$-3-keto-steroid-17α-yl)propionic acid lactones of the androstane series represented by the general partial formula

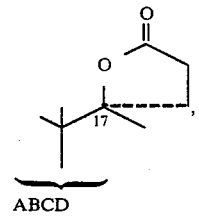

wherein ABCD represents an optionally substituted cyclopentanophenanthrene steroid molecule skeleton, from corresponding 17α-(3-hydroxypropynyl)-17β-hydroxy steroids, comprises reducing the latter to the 17α-(3-hydroxypropenyl)17β-hydroxy steroid, effecting ring closure to the lactol, and subsequently oxidizing with chromic acid to the lactone.

12 Claims, No Drawings

PROCESS FOR THE PREPARATION OF 3-(Δ⁴-3-KETOSTEROID-17α-YL)PROPIONIC ACID LACTONES

BACKGROUND OF THE INVENTION

The present invention concerns a new method of forming steroidal-17yl-propiolactones.

It is known that $\Delta^4$-3-ketosteroid-17-propiolactones, for example, 3-(17β-hydroxy-4-androsten-3-one-17α-yl)propionic acid lactone, can be produced by homogeneous hydrogenation of the corresponding 17α-hydroxypropynyl-$\Delta^4$-3-keto steroids to obtain the corresponding 17α-hydroxypropyltestosterones, and subsequent Jones oxidation in a two-stage reaction (U.S. Pat. No. 4,129,564).

Hydrogenation with homogeneous catalysts, e.g. tris(triphenyl)phosphine rhodium chloride, in addition to high catalyst cost, has the disadvantage that rhodium, objectionable from a toxicological viewpoint anyway, can be removed from the subsequent stages only with great expenditure.

SUMMARY OF THE INVENTION

Accordingly, it is an object of the present invention to provide a method for preparing $\Delta^4$-3-keto steroid propiolactones using a hydrogenation catalyst, which method does not exhibit the foregoing disadvantages or possesses them to a lesser degree.

Upon further study of the specification and appended claims, further objects and advantages of this invention will become apparent to those skilled in the art.

It has now been found surprisingly that an intermediarily formed propenol 17α-(3-hydroxypropenyl)-17β-hydroxy steroid can be rearranged, in the presence of Raney nickel, into the corresponding lactol which can then be further oxidized to the lactone without separation. Thus, this invention relates to a process for the preparation of 3-($\Delta^4$-3-ketosteroid-17α-yl)propionic acid lactones of the androstane series having the partial formula:

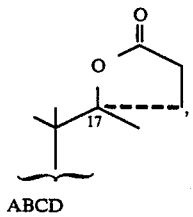

ABCD wherein ABCD represents the optionally substituted cyclopentanophenanthrene steroid molecular skeleton, from the corresponding 17α-(3-hydroxypropynyl)-17β-hydroxy steroids of the partial formula:

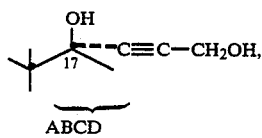

ABCD wherein ABCD is as defined above, comprising intermediarily hydrogenating the 17α-(3-hydroxypropynyl)-17β-hydroxy steroid on Raney nickel to form the 17α-(3-hydroxypropenyl)17β-hydroxy steroid, then treating the latter with 2–20 times the amount of Raney nickel as compared with the quantity previously utilized during the hydrogenation, and thereafter oxidizing with chromic acid.

DETAILED DISCUSSION

The allyl rearrangement on Raney nickel of this invention has not been disclosed heretofore. Such a smooth reaction could not be expected with molecules of such complexity as the present steroids. Rather, reaction of the $\Delta^4$- or $\Delta^{20}$-double bond would have been expected with Raney nickel.

It is believed that the process of this invention proceeds schematically in accordance with the following scheme:

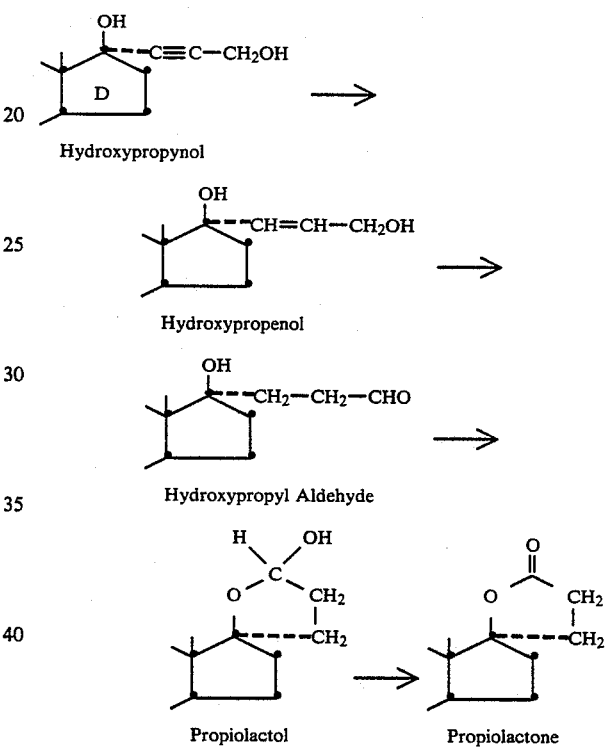

The process of this invention is suitably conducted by dissolving the 17α-(3-hydroxypropynyl)-17β-hydroxy steroid in a suitable reaction compatible solvent and hydrogenating on Raney nickel with hydrogen until saturation has been attained. For the hydrogenation, suitable amounts of catalyst include 0.05–0.2 times the quantity of steroid employed. Suitable Raney nickel is of commercial quality, for example, B 113 Z and B 115 Z of Degussa, Frankfurt/Main. The hydrogenation can be carried out under normal pressure, but it proceeds correspondingly faster under slightly raised pressure in the range of 1 to 5 bar. The hydrogenation is carried out at 0° to 50° C. and is stopped when one equivalent of hydrogen has been absorbed.

Subsequently, the reaction mixture is combined with a larger amount of Raney nickel, e.g., the same previously also used for the hydrogenation. A suitable amount is about 2–20 times the previously added quantity. After adding the additional catalyst, the reaction mixture is stirred for some time, the time period being dependent on the reaction temperature, e.g., at least one hour. °C.-reflux, at which stirring is conducted. At temperatures of around 0° C., the reaction time is about 8 hours; at the temperature of the boiling reaction mixture, the time is about one-quarter hour. However, the stirring step can suitably be conducted at room temperature, in which case a reaction period of 1-3 hours is satisfactory.

Subsequently, the reaction mixture, after removal of the catalyst by filtration, is treated with chromic acid in a suitable reaction medium, such as glacial acetic acid, sulfuric acid/acetone, or sulfuric acid/water, e.g., using Jones' solution. The reaction is advantageously performed by adding the chromic acid gradually to the reaction mixture under cooling conditions. Typical amounts of chromic acid are 1-1.5 equivalents of the steroid. Typical temperature/reaction times are 0° to 20° C. and 10 minutes to one hour.

Suitable solvents for the hydrogenation and the subsequent rearrangement reaction include aprotic solvents, since secondary reactions, such as reduction of the $\Delta^4$-double bond, would occur in a protonic solvent, such as in an alcohol. Examples of suitable aprotic solvents include acetone, methyl isobutyl ketone, benzene, toluene, dioxane, tetrahydrofuran, dimethylformamide, or a mixture thereof, etc.

The reaction product is worked up by following operating procedures customarily employed in chemistry, such as, for example, extraction or concentration under vacuum. The resultant crude product is purified as usual, for example by recrystallization or chromatography.

The process of this invention has the advantage, in particular, that it can be performed in a simple way on an industrial scale.

The $17\alpha$-(3-hydroxypropynyl)-$17\beta$-hydroxy steroid utilized as the starting material can be substituted as desired in the A, B, C, and D rings, as long as the substituents are inert with respect to the reactants. Thus, for example, methyl groups can be present in the 1-, 6-, and 16-positions, and methylene groups can be in the 1,2-, 6,7-, and 15,16-positions and oxogroups in the 3- and/or 11-position. The $17\alpha$(3-hydroxypropenyl)-$17\beta$-hydroxy steroids may be unsaturated for example in the 1(2)-, 4(5)-, 5(6)-, 6(7)-, 9(11)- and 15(16)-position. 3-Hydroxy-$\Delta^5$-steroids, 3,5-dihydroxysteroids and ketals or enolethers of 3-keto-$\Delta^4$-steroids are converted to 3-keto-$\Delta^4$-steroids during the reaction.

All starting materials needed are known and are preparable from known 17-oxosteroids, e.g., under the conditions described in example 3 herein.

Preferred starting materials are those of the formula

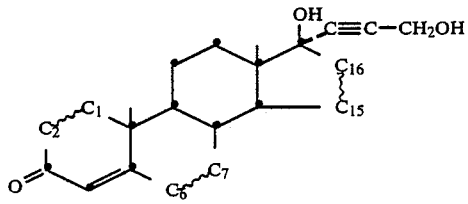

wherein

—$C_2$~$C_1$—, —$C_8$~$C_7$— and —$C_{15}$~$C_{16}$— are

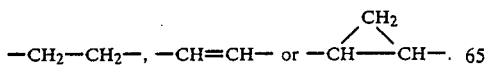

The compounds producible by the process of this invention are useful as intermediates for the synthesis of pharmacologically active steroids or other compounds useful as such intermediates.

For example, the compounds of the general formula

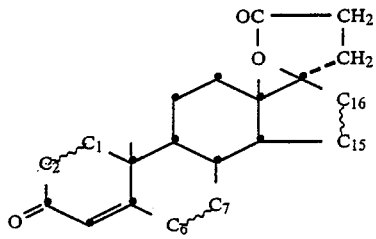

wherein

—$C_2$~$C_1$—, —$C_8$~$C_7$ and/or —$C_{15}$~$C_{16}$ are

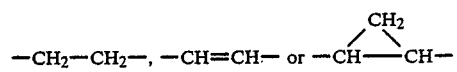

can all be used to prepare known aldosterone antagonists. (U.S. Pat. Nos. 3,013,012, 3,966,714 and 4,129,564 and U.S. patent applications No. 516,391—filed July 22, 1983—and No. 546,352—filed Oct. 18, 1983 whose disclosures are incorporated by reference herein).

In addition, the final products can be used by routine combination of known reactions of steroids to produce a very wide variety of other steroids having various uses. See, e.g., *Steroid Reactions*, C. Djerassi, Ed., Holden-Day, Inc., San Francisco, 1963, whose disclosure is incorporated by reference herein. The final products can also be used to prepare each other and the starting materials from which they were prepared.

For example, the specific lactones mentioned above can be conventionally converted into the corresponding know aldosterone antagonists, e.g., 3-(7$\alpha$-acetylthio-17$\beta$-hydroxy-3-oxo-4-androsten-17$\alpha$-yl)propionic acid lactone (spironolactone) by dehydrogenation in the 6-position according to J. Org. Chem. 24:1109 (1959) and subsequent reaction with thioacetic acid according to U.S. Pat. No. 3,013,012 for example. Analogously, the conventional 6$\beta$,7$\beta$;15$\beta$,16$\beta$-dimethylene-3-oxo-4-androsten[17-($\beta$-1')spiro-5']perhydrofuran-2'one (DOS No. 2,652,761) can be obtained from 3-(17$\beta$-hydroxy-6$\beta$,7$\beta$;15$\beta$,16$\beta$-bis-methylene-4-androsten-3-on-17$\alpha$-yl)propiolactone.

Without further elaboration, it is believed that one skilled in the art can, using the preceding description, utilize the present invention to its fullest extent. The following preferred specific embodiments are, therefore, to be considered as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

3.0 g of 17$\alpha$-(3-hydroxypropynyl)-17$\beta$-hydroxy-4-androsten-3-one is hydrogenated in 50 ml of tetrahydrofuran with 0.3 g of Raney nickel (Degussa, type B 113 Z) for 1.5 hours. Another 3 g of Raney nickel is added to the reaction solution, and the latter is stirred for 3 hours at room temperature, filtered, and combined with 2.5 ml of Jones solution (prepared from 4.6 ml of concentrated sulfuric acid and 5.4 mg of chromium trioxide, filled up to 20 ml with water) at 0° C. After 5 mintes, the excess chromic acid is combined with methanol, 100 ml of ice water is added, and the reaction mixture is extracted with methylene choride. The extract is washed with water, dried over magnesium sulfate, and evaporated. The oily residue is briefly heated with 5 ml of diisopropyl ether, thus obtaining crystallization, and the product is evaporated to dryness under vacuum, thus producing 2.4 g of 3-(17β-hydroxy-4-androsten-3-on-17α-yl)propionic acid lactone, mp 153°–155° C.

EXAMPLE 2

3.0 g of 17α-(3-hydroxypropynyl)-17β-hydroxy-4-androsten-3-one is hydrogenated in 50 ml of acetone with 0.3 g of Raney nickel (Degussa, type B 115 Z). After adding another 2 g of Raney nickel, the mixture is refluxed for 15 minutes, cooled to room temperature, filtered, and combined with 2.5 ml of Jones solution at 0° C. The reaction mixture is worked up as described in Example 1, yielding 2.3 g of 3-(17βhydroxy-4-androsten-3-on-17α-yl)propionic acid lactone, mp 152°–156° C.

EXAMPLE 3

5.0 g of 17α-(3-hydroxypropynyl-17β-hydroxy-6,7;15,16-bis-methylene-4-androsten-3-one is hydrogenated in 50 ml of toluene with 0.3 g of Raney nickel (Dequssa, type B 115 Z). After adding another 2 g of Raney nickel, the mixture is refluxed for 20 minutes, evaporated, the residue taken up in acetone, and oxidized with 2.5 ml of Jones reagent at 0° C. After a working-up process as described in Example 1, 4.8 g of 3-(17β-hydroxy-6,7;15,16-bis-methylene-4-androsten-3-on-17α-yl)propionic acid lactone is obtained, mp 193°–195° C.

Preparation of starting material:

1.0 g of 3β,5β-dihydroxy-6,7β;15,16β-dimethyleneandrostan-17-one ("Angew. Chem." 94:718 [1982]) is heated in 10 ml of dimethylformamide with 2 g of pyridinium dichromate for 7 hours to 70° C., stirred into 100 ml of ethyl acetate, filtered over sodium sulfate, the filtrate is washed with dilute sulfuric acid, water, sodium bicarbonate solution, dried, and evaporated. The residue (0.76 g) yields, after crystallization from acetone, 0.3 g of colorless crystals, mp 229° C.

[α]$_D$ = −225.7°

2.17 g of 6,7;15,16-dimethyleneandrost-4-ene-3,17-dione is combined in 20 ml of tetrahydrofuran under nitrogen with 8.84 g of potassium ethylate and, under agitation, 2 ml of propargyl alcohol in 2 ml of tetrahydrofuran is added dropwise thereto. After 30 minutes at room temperature, the reaction mixture is neutralized with acetic acid, concentrated, water is added, and the mixture is extracted with methylene chloride; the latter is dried over magnesium sulfate and evaporated. The residue (2.68 g) yields, after chromatography on silica gel, 440 mg of colorless crystals, mp 165° C.

[α]$_D$ = −311.4° (chloroform).

EXAMPLE 4

1.0 g of 17α-(3-hydroxypropynyl)-3β,5β,17β-trihydroxy-6,7;15,16-bis-methyleneandrostane ("Angew. Chem." 94:718 [1982]) is hydrogenated in 25 ml of tetrahydrofuran with 0.2 g of Raney nickel. After adding 2.5 g of Raney nickel, the mixtue is stirred for 30 minutes, filtered, and combined at 0° C. with excess Jones solution. The reaction mixture is worked up as described in Example 1, yielding 0.5 g of 3-(17β-hydroxy-6,7;15,16-bis-methylene-4-androsten-3-on-17α-yl)propionic acid lactone, mp 190°–194° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 3-(Δ$^4$-3-ketosteroid-17α-yl)propionic acid lactone of the androstane series of the partial formula:

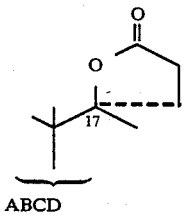

wherein ABCD represents an optionally substituted cyclopentanophenanthrene steroid, comprising hydrogenating the corresponding 17α-(3-hydroxypropynyl)-17β-hydroxy steroid of the partial formula:

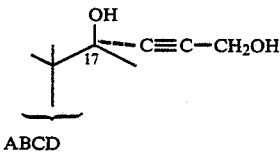

with an effective amount of Raney nickel to form the corresponding 17α-(3-hydroxypropenyl)-17β-hydroxy steroid, treated the latter with 2–20 times the amount of Raney nickel used in the preceding hydrogenation, and thereafter oxidizing the resultant product with chromic acid.

2. A process of claim 1 carried out in an aprotic solvent.

3. A process of claim 2 wherein the aprotic solvent is acetone, methyl isobutyl ketone, benzene, toluene, dioxane, tetrahydrofuran, dimethylformamide, or a mixture thereof.

4. A process of claim 1 wherein the first stage of hydrogenation is carried out with 0.05–0.2 wt % of Raney nickel based on the amount of steroid.

5. A process of claim 1 wherein the first stage hydrogenation is carried out at a pressure of 1–5 bar.

6. A process of claim 1 wherein the second stage Raney nickel treatment is carried out at 0° C. to reflux temperature for 8–0.25 hours.

7. A process of claim 1 wherein the chromic acid reaction is conducted in glacial acetic acid, sulfuric acid/acetone, or sulfuric acid/water.

8. A process of claim 1 wherein the chromic acid reaction is conducted in Jones solution.

9. A process of claim 1 wherein the starting material androstene is substituted by 1-, 6- or 16-methyl or 1,2-, 6,7-, or 15,16-methylene.

10. A process of claim 1 wherein the starting androstene is unsubstituted.

11. A process of claim 1 wherein the starting androstene is substituted by 6β,7β,15β,16β-bismethylene.

12. A process of claim 1 wherein the chromic acid treatment is conducted in situ after removal of the Raney nickel catalyst from the reaction medium.

* * * * *